United States Patent
Brooks

[11] Patent Number: 6,126,589
[45] Date of Patent: Oct. 3, 2000

[54] THERAPEUTIC MAGNETIC SHEET

[75] Inventor: David H. Brooks, Old Westbury, N.Y.

[73] Assignee: Brooks Industries of Long Island, Old Westbury, N.Y.

[21] Appl. No.: 09/302,845

[22] Filed: Apr. 30, 1999

Related U.S. Application Data

[60] Provisional application No. 60/083,764, May 1, 1998.

[51] Int. Cl.$^7$ .................................................... A61B 17/52
[52] U.S. Cl. .................................................................. 600/15
[58] Field of Search .......................................... 600/9–15

[56] References Cited

U.S. PATENT DOCUMENTS

| | | |
|---|---|---|
| 4,162,672 | 7/1979 | Yazaki . |
| 4,489,711 | 12/1984 | Latzke . |
| 4,549,532 | 10/1985 | Baermann . |
| 5,017,185 | 5/1991 | Baermann . |
| 5,259,892 | 11/1993 | Kubota . |
| 5,277,692 | 1/1994 | Ardizzone . |
| 5,304,111 | 4/1994 | Mitsuno et al. . |
| 5,336,498 | 8/1994 | Snider . |
| 5,514,072 | 5/1996 | Ardizzone . |
| 5,538,495 | 7/1996 | Ardizzone . |
| 5,984,856 | 6/1998 | Love ........................................ 600/15 |

FOREIGN PATENT DOCUMENTS

| | | |
|---|---|---|
| 1215110 | 4/1960 | France . |
| 2371916 | 11/1976 | France . |
| 59-7475 | 1/1981 | Japan . |

*Primary Examiner*—John P. Lacyk
*Attorney, Agent, or Firm*—Shaw Pittman

[57] ABSTRACT

A flexible therapeutic magnetic sheet, e.g., fabricated from randomly-distributed ferromagnetic particles mixed in a plastic resin and formed into a sheet. A magnetic field is applied to the sheet to permanently magnetize the sheet according to a spiral pattern. The spiral pattern comprises a Northern pole spiral interlaced with a spiral pole Southern. When the therapeutic sheet is applied to the skin of a person or an animal, the ions and electrolytes in the blood traverse alternating polarity magnetic fields. The alternating polarity magnetic fields exert magnetic forces in alternating directions on the ions and electrolytes in the blood, thus generating heat in the blood vessels and increasing the blood circulation.

16 Claims, 3 Drawing Sheets

THERAPEUTIC MAGNETIC SHEET

The present application claims priority from Provisional Patent Application Ser. No. 60/083,764, filed May 1, 1998.

BACKGROUND

1. Field of the Invention

The present invention relates to flexible magnetic sheets, which are applied to the skin of persons or animals for therapeutic or analgesic purposes.

2. Background Of The Invention

Magnetic therapeutic plasters are described in U.S. Pat. No. 4,489,711 to Latzke ("Latzke"), which is incorporated by reference herein. The magnetic poles in FIG. 1 of Latzke are disposed in alternating rows of "+" and "−" (i.e., North and South) poles. Latzke implemented the invention on magnetic rubber sheets having a thickness of 0.5 to 1.5 mm thick, with the magnetic poles 5–10 mm apart, and a magnetic field strength of 50 to 10,000 gauss, preferably, 400 to 2,000 gauss. The examples in Latzke describe the beneficial effects of treatment with the magnetic plasters.

U.S. Pat. No. 4,549,532 to Baermann ("Baermann") discloses several different geometries for a flexible magnetic sheet, including circular strips of alternating polarities (FIG. 1), triangular strips (FIG. 2), rectangular or square strips (FIG. 3) and octagonal strips (FIG. 4). U.S. Pat. Nos. 5,277,692, 5,538,495 and 5,514,072 to Ardizzone disclose a flexible magnetic pad in which alternating N/S magnets spiral out from a central core such that triangular wedges of N/S alternating magnets radiate from the central core. U.S. Pat. No. 5,304,111 to Mitsuno et al. disclose a flexible magnetic sheet in which the N/S magnetic poles are disposed in a checkerboard pattern. Other U.S. patents of interest include U.S. Pat. Nos. 4,162,672 to Yazaki, U.S. Pat. No. 5,336,498 to Snider, U.S. Pat. No. 5,017,185 to Baermann and U.S. Pat. No. 5,259,892 to Kubota. Foreign patents of interest include French Patent No. 1,215,110 to Tanaka, Japanese Laid-Open Patent Application No. 56-7405 to Miyake, and French Patent 2,371,916 to Van Den Bulke.

DESCRIPTION OF THE INVENTION

Figure 1:
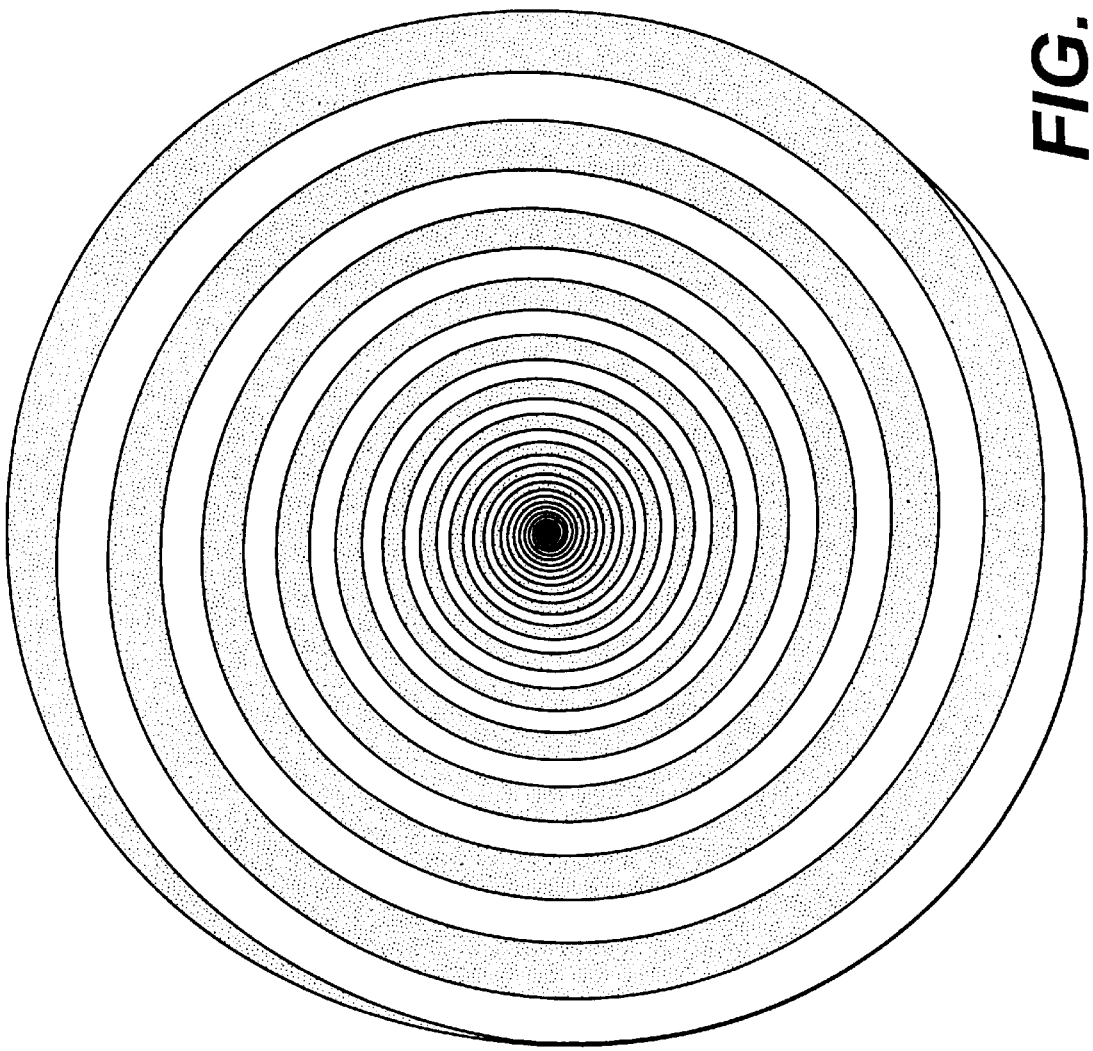
FIG. 1 is a schematic representation of a first preferred spiral pattern of North/South magnetization used in the present invention.
Figure 2:
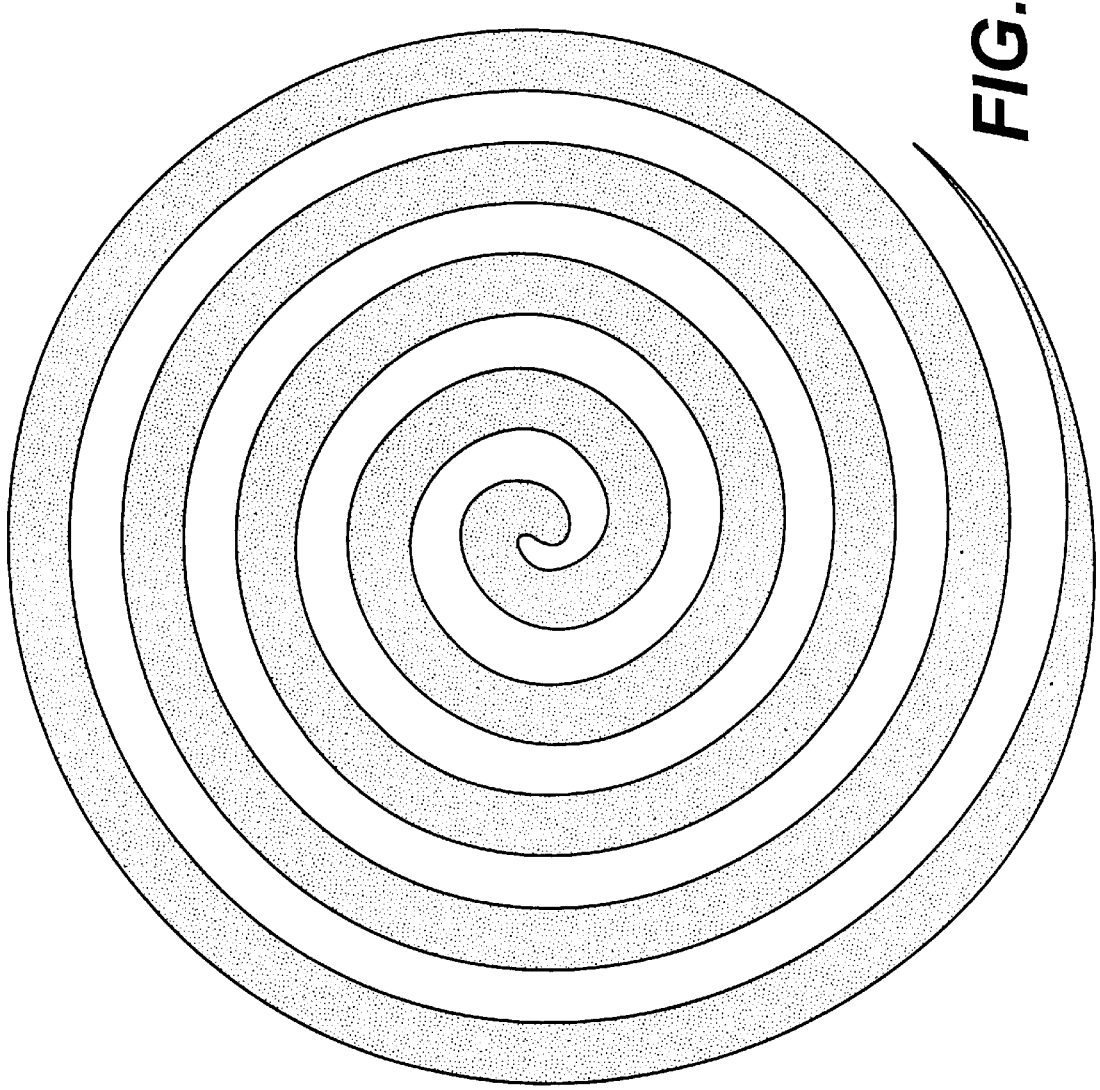
FIG. 2 is a schematic representation of a second preferred spiral pattern of North/South magnetization used in the present invention.
Figure 3:
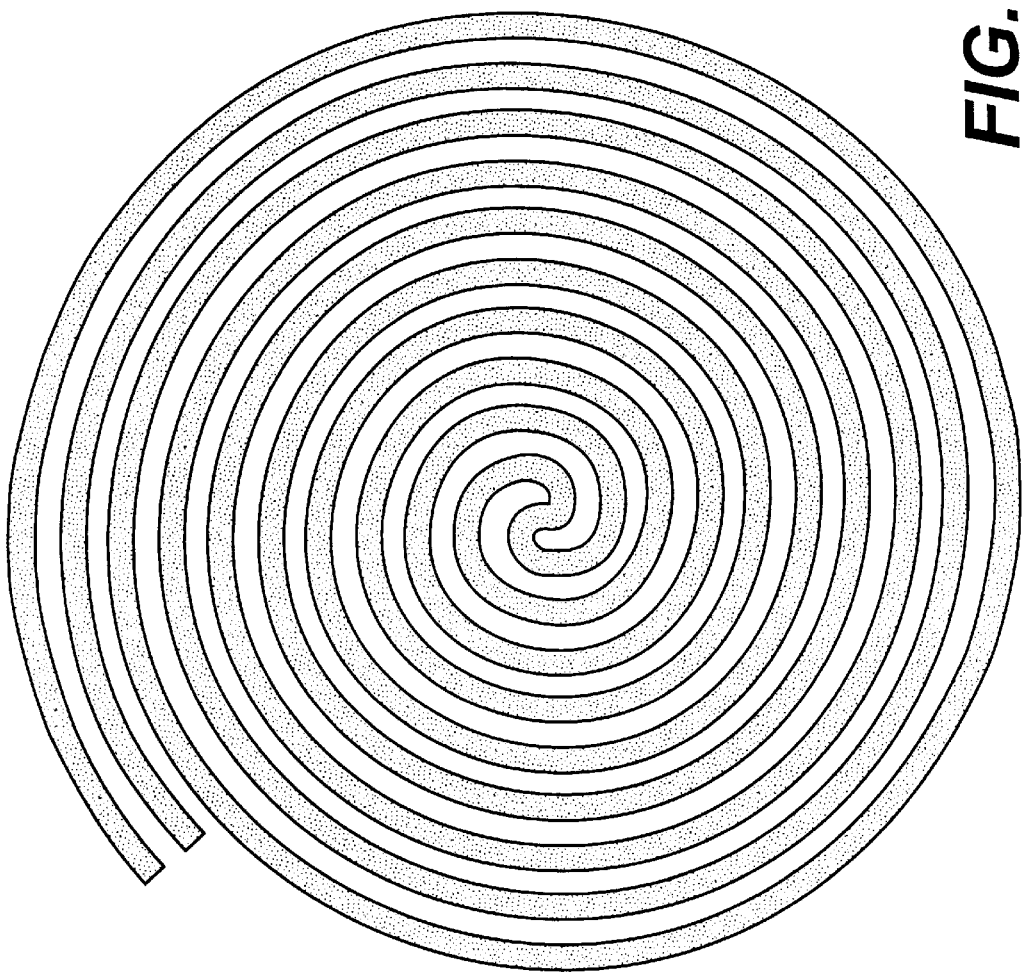
FIG. 3 is a schematic representation of a third preferred spiral pattern of North/South magnetization used in the present invention.

The present invention is fabricated from randomly-distributed ferromagnetic particles mixed into a plastic resin, and formed into a disk-shaped sheet. A magnetic field is then applied to permanently magnetize the disk-shaped sheet according to the desired spiral pattern. Examples of such patterns are shown schematically in FIGS. 1, 2 and 3. The magnetic field may be applied using electromagnets or permanent magnets. In FIGS. 1, 2 and 3, the black areas represent, e.g., Northern poles (defined herein as poles oriented such that the vector representing the magnetic field is out of the surface of the sheet), and the white areas represent the Southern magnetic poles (defined herein as poles oriented such that the vector representing the magnetic field is directed into the surface of the sheet).

The magnetized plastic sheet may be 0.2 to 5 mm thick, preferably 0.5 to 2.0 mm thick. The field strength of the magnetic poles can range from 50 to 10,000 gauss, but preferably range from 400 to 2,000 gauss.

The patterns shown in FIGS. 1 and 2 have only one Northern pole (the black area) and one Southern pole (the white area). The pattern shown in FIG. 3 has one Northern pole (the black area) that reverses at the center and is interlaced with two Southern poles (white areas). In all three examples shown in the Figures, each pole starts out near the center of the disk, and spirals outwards towards the circumference of the disk, with the Southern spiral pole(s) interlaced with the Northern spiral pole. Blood cells and other blood components crossing the patterns of FIGS. 1, 2 or 3 would experience a maximum exposure to alternating North and South magnetic fields.

As explained in U.S. Pat. No. 5,277,692 to Ardizzone (the "Ardizzone patent"), human or animal blood contains ions and electrolytes, i.e., blood contain charged particles. When a magnetic sheet manufactured according to the present invention is applied to the skin of a person (or an animal), the magnetic fields produced by the North and South poles into or out of the skin of the person (or animal) penetrate into the person (or animal), subjecting the blood therein to a pattern of alternating magnetic fields. When charged particles move (i.e., when the blood flows, carrying the ions and electrolytes) through a magnetic field, the magnetic field acts upon the particles with a magnetic force proportional to (1) the strength of the magnetic field and (2) the component of velocity at which the particles travel relative to the magnetic field which is perpendicular to the magnetic field.

For a given direction of blood flow, the direction of the magnetic force is determined by the direction of the magnetic field, i.e., the force experienced by an ion in the blood under a North pole magnet would be opposite to the force experienced under a South pole magnet. Thus ions and electrolytes in the blood traveling through alternating North and South poles experience alternating magnetic forces, which serve to push the charged particles to alternate sides of the blood vessels. According to the results of clinical trials filed in conjunction with the prosecution of the Latzke patent, this exposure to alternating North/South magnetic fields results in effective therapeutic and analgesic treatment, due at least in part to the heat generated in the blood vessels themselves as a result of the alternating motion, and as well as to increased blood circulation resulting from the alternating motion.

The spiral patterns shown in FIGS. 1, 2 or 3 differ from the pattern shown in the Ardizzone patent because in Ardizzone each spiral contains alternating North and South poles, whereas in the present invention, each spiral is either a North pole in its entirety, or a South pole in its entirety. The pattern of the present invention is less complex than the pattern of disclosed in Ardizzone, and is therefore more easily manufactured.

The spiral pattern of the present invention differs from the concentric circle pattern disclosed in FIG. 1 of Baermann most significantly in the center. A comparison of FIGS. 1, 2 or 3 herein to Baermann's FIG. 1 shows that a blood vessel crossing near the center of the spiral pattern would experience a greater number of alternating North/South polarities than a blood vessel crossing near the center of Baermann's concentric circle pattern. Accordingly, the therapeutic and analgesic effects of the present invention are more effective for the area under the central portion of the spiral pattern of the present invention, compared to the central area of Baermann's circular pattern.

FIG. 1 shows a spiral pattern in which the width of the North and South poles spirals varies as the spiral moves outward from the center, i.e., the spirals are relatively narrow at the center, and increase in monotonically in width towards the periphery. FIG. 2 shows a spiral pattern in which the width of the North and South spirals is constant. FIG. 3 shows spiral patterns similar to the patterns shown in FIG. 2, but with one pole, e.g., the North pole, is a double spiral that reverses at the center, and the opposite polarity (e.g., the South pole) having two spirals that start at the center and are interlaced with the reversing North pole double spiral.

Although the present invention has been described with respect to the spiral pattern shown in FIGS. 1, 2 or 3, other spiral patterns may also be used. To one of ordinary skill in the art, the present invention may be practiced with many variations and modifications of the embodiment described herein, in light of the above disclosure.

What I claim is:

1. A flexible therapeutic sheet 0.2 to 5 mm thick comprising a North pole spiral interlaced with a South pole spiral, wherein the magnetic field strength of the North pole and the South pole range from 50 gauss to 10,000 gauss.

2. The flexible therapeutic sheet of claim 1, wherein the magnetic field strength of the North pole spiral and the South pole spiral range from 400 gauss to 2,000 gauss.

3. The flexible therapeutic sheet of claim 1, wherein the sheet is approximately 0.5 to 2.0 mm thick.

4. The flexible therapeutic sheet of claim 1, wherein the North and South pole spirals have a constant width.

5. The flexible therapeutic sheet of claim 1, wherein the North and South pole spirals have a variable width.

6. The flexible therapeutic sheet of claim 5, wherein the North and South pole spirals are relatively narrow near the center of the spirals and increase monotonically in width towards the periphery of the spirals.

7. A method for manufacturing a flexible therapeutic sheet comprising the steps of:

(a) providing a flexible sheet 0.2 mm to 5 mm thick with randomly oriented ferromagnetic particles embedded therein; and (b) applying a magnetic field in a first direction relative to the flexible sheet so as to permanently magnetize a first spiral pattern in the flexible sheet in a first orientation; and (c) applying a magnetic field in a second direction to the flexible sheet so as to permanently magnetize a second spiral pattern interlaced with the first spiral pattern in the flexible sheet in a second orientation opposite to the first orientation.

8. The method of claim 7, wherein the flexible sheet is magnetized such that the magnetic field strength of the North pole and the South pole range from 400 gauss to 2,000 gauss.

9. The method of claim 7, wherein the sheet is approximately 0.5 to 2.0 mm thick.

10. The method of claim 7, wherein the flexible sheet is magnetized such that the North and South pole spirals have a constant width.

11. The method of claim 7, wherein the flexible sheet is magnetized such that the North and South pole spirals have a variable width.

12. The method of claim 11, wherein the flexible sheet is magnetized such that the North and South pole spirals are relatively narrow near the center of the spirals and increase monotonically in width towards the periphery of the spirals.

13. A flexible therapeutic sheet 0.2 to 5 mm thick comprising a double North pole spiral that reverses at the center of the spiral interlaced with two South pole spirals, wherein the magnetic field strength of the North pole spiral and the South pole spiral range from 50 gauss to 10,000 gauss.

14. The flexible therapeutic sheet of claim 13, wherein the magnetic field strength of the North pole spiral and the South pole spirals range from 400 gauss to 2,000 gauss.

15. The flexible magnetic sheet of claim 13, wherein the North pole spiral has a constant width.

16. The flexible magnetic sheet of claim 13, wherein the North pole spiral has a variable width.

* * * * *